US009427354B2

(12) United States Patent
Zysler et al.

(10) Patent No.: US 9,427,354 B2
(45) Date of Patent: Aug. 30, 2016

(54) MATERIAL FOR MEDICAL USE COMPRISING NANOPARTICLES WITH SUPERPARAMAGNETIC PROPERTIES AND ITS UTILIZATION IN SURGERY

(75) Inventors: Roberto Zysler, Rio Negro (AR); Alejandro Berra, Ciudad Autónoma de Buenos Aires (AR); Pablo Gurman, Richardson, TX (US); Orlando Hector Auciello, Garland, TX (US); Mario Joaquin Saravia, Buenos Aires (AR)

(73) Assignee: NANOPHTHALMICS, LLC, Milford, Kent County, DE (US)

( * ) Notice: Subject to any disclaimer, the term of this patent is extended or adjusted under 35 U.S.C. 154(b) by 590 days.

(21) Appl. No.: 13/825,176

(22) PCT Filed: Sep. 9, 2011

(86) PCT No.: PCT/US2011/051009
§ 371 (c)(1),
(2), (4) Date: May 6, 2013

(87) PCT Pub. No.: WO2012/039960
PCT Pub. Date: Mar. 29, 2012

(65) Prior Publication Data
US 2013/0225906 A1    Aug. 29, 2013

(30) Foreign Application Priority Data

Sep. 20, 2010  (AR) .............................. P20100103421

(51) Int. Cl.
*A61F 9/007*    (2006.01)
*A61K 9/00*     (2006.01)
(Continued)

(52) U.S. Cl.
CPC ........... *A61F 9/007* (2013.01); *A61F 9/00727* (2013.01); *A61K 9/0048* (2013.01);
(Continued)

(58) Field of Classification Search
CPC ...... A61F 2/14; A61F 2/147; A61F 9/00727; A61K 9/0051; A61K 9/5094; A61K 9/0048; A61L 31/14; A61N 2/00; A61N 2/002; A61N 2/004; A61N 2/06
See application file for complete search history.

(56) References Cited

U.S. PATENT DOCUMENTS 6,135,118 A * 10/2000 Dailey .......................... 128/898
2005/0203333 A1    9/2005 Dailey et al.
(Continued)

FOREIGN PATENT DOCUMENTS

EP    1852107 A1    11/2007
ES    2132029 A1    8/1999
(Continued)

OTHER PUBLICATIONS

International Search Report Date Jun. 21, 2012.
(Continued)

*Primary Examiner* — Charles M Marmor, II
*Assistant Examiner* — Carrie R Dorna
(74) *Attorney, Agent, or Firm* — Norris McLaughlin & Marcus PA

(57) ABSTRACT

This invention relates to a material for medical use that comprises biocompatible nanoparticles having superparamagnetic properties, where the superparamagnetic properties of said nanoparticles are used to localize their action on a determined space or tissue. In particular, said nanoparticles having superparamagnetic properties are composed of magnetite. The material according to the invention has various applications, both in surgical and in therapeutic treatments.

4 Claims, 4 Drawing Sheets

(51) Int. Cl.
*A61K 9/50* (2006.01)
*A61K 9/51* (2006.01)
*A61L 27/04* (2006.01)
*A61L 27/54* (2006.01)

(52) U.S. Cl.
CPC .......... *A61K9/0051* (2013.01); *A61K 9/5094* (2013.01); *A61K 9/5115* (2013.01); *A61K 9/5146* (2013.01); *A61L 27/042* (2013.01); *A61L 27/54* (2013.01); *A61L 2300/44* (2013.01); *A61L 2400/06* (2013.01); *A61L 2400/12* (2013.01); *A61L 2430/16* (2013.01)

(56) References Cited

U.S. PATENT DOCUMENTS

| | | | |
|---|---|---|---|
| 2006/0025713 A1* | 2/2006 | Rosengart et al. | 604/5.02 |
| 2006/0142632 A1* | 6/2006 | Meretei | A61B 17/3207 600/12 |
| 2010/0228237 A1 | 9/2010 | Chung et al. | |
| 2011/0060320 A1* | 3/2011 | Aharon-Attar | 606/4 |
| 2011/0256066 A1 | 10/2011 | Bae et al. | |

FOREIGN PATENT DOCUMENTS

| | | |
|---|---|---|
| JP | 2009114066 A | 5/2009 |
| JP | 2009524631 A | 7/2009 |
| JP | 2009534350 A | 9/2009 |
| WO | 2004006765 A1 | 1/2004 |
| WO | 2007085804 A1 | 8/2007 |
| WO | 2010/074539 A2 | 7/2010 |

OTHER PUBLICATIONS

J. Wen, et al., "Use of superparamagnetic microbeads in tracking subretinal injections", Molecular Vision, 11, pp. 256-262, 2005.

M.M. Lin, et al, "Development of Superparamagnetic Iron Oxide Nanoparticles (SPIONS) for Translation to Clinical Applications", IEEE Transactions of NanoBioscience, vol. 7, Issue 4, pp. 298-305, 2008.

Y. Ishizaka, et al—Japanese Patent Abstract retrieved Nov. 27, 2015—XP002751530.

J. M. Vargas, et al., "Tailloring the size in colloidal iron oxide magnetic nanoparticles", Nanotechnology, 16, pages 1474-1476, 2005, UK.

EP Search Report for corresponding application 11827214.5 dated Dec. 8, 2015.

* cited by examiner

MATERIAL FOR MEDICAL USE COMPRISING NANOPARTICLES WITH SUPERPARAMAGNETIC PROPERTIES AND ITS UTILIZATION IN SURGERY

This application is a 371 application of PCT/US2011/051009 filed Sep. 9, 2011, which claims foreign priority benefit under 35 U.S.C. §119 of Argentina Patent application 20100103421 filed Sep. 20, 2010.

This invention relates to a material for medical use that comprises nanoparticles having superparamagnetic properties, where said nanoparticles are used to localize their action on a determined space or tissue. In particular, said nanoparticles having superparamagnetic properties are composed of an iron oxide, the latter being, among others and preferably, magnetite.

In particular embodiments, the material for medical use of this invention comprises superparamagnetic nanoparticles adhered to one therapeutically active substance, or to more than one, or to one substance showing a radiant activity, or more than one of the latter substances.

In a preferred embodiment, the material is used for the treatment of retinal detachment.

BACKGROUND OF THE INVENTION

When, in the course of a pathological process or in predisposed individuals, the retina breaks, a retinal detachment may take place.

Retinal detachment is a disorder that inevitably led to blindness until 1918, when Tules Gonin proposed the ignipuncture treatment (puncturing and cauterizing) as a first effective treatment. Not only that, but, and perhaps more importantly, he introduced the conception that retinal detachment is cured when the occlusion of the tearing that created the detachment is achieved. In the 1950's, Charles Schepens proposes, as a means to achieve said occlusion, the placement of a circular explant that, sutured to the sclera, creates an indentation in the area corresponding to the tear. That same decade, a method for definitive sealing was proposed. The method comprises the creation of local inflammation in both the retina and the choroids surrounding the tear, this leading, eventually, to an adherence stronger than the physiological one. In order to achieve that adherence, Meyer-Schwickerath proposed the use of photocoagulation. A decade later, Lincoff achieved the same effect utilizing localized cold, by means of the method known as cryopexy. In 1971, Robert Machemer and Golham Peyman, each one of them working separately, publish the first works using vitrectomy to repair detached retinas. Said methodology consists of tackling a retina from inside, entering the eye through the pars plana and extracting the vitreous that is tractioning the retina. This permitted the advent of the utilization of internal tamponading to replace the vitreous, such as silicone oil (originally disclosed by Cibis in 1962, but whose use extended with vitrectomy); the exchange of fluid by gas (Steve Charles, 1977) and perfluorocarbon (Stanley Chang, 1987). These have been the fundamental advances in retinal detachment surgery and, up until today, have been the pillars for the treatment of that problem.

Internal tamponades are used to position and maintain the retina applied against the eye inner wall, when a retinal tear caused the detachment.

The way to achieve a permanent adherence between the detached retina and the pigment epithelium (PE) wall is to provoke a localized inflammation by means of a laser beam or another thermal source. The inflammation creates an adherence between retina and PE that is much stronger than the physiological adherence. However, said adherence can only be achieved by maintaining both parts in contact in the course of a process that may last several days before consolidation. Because of that, the use of tamponades is necessary.

Preferably, tamponades are used temporarily. Liquid perfluorocarbon is a heavy and transparent liquid used during surgery and has to be removed before the surgery is finished.

Silicone oil, with various densities, may be left inside the eye for periods of weeks or even months. It is introduced during one surgical operation and is extracted with another ad hoc operation, Air was the first element used when fluid was exchanged by gas. However, air remains inside the eye for 48 hours only, this time being insufficient to permit a definitive attachment of a retina to its eye wall. Consequently, gas tamponades with special gases having longer reabsorption periods are used.

Gas tamponades are based on the use of gas formulations (for example, C3FS and SFS in variable dilutions) permitting that the gas bubble maintain a useful volume inside the eye for a long time (time ranging from few days to several weeks).

Both gas tamponades and silicone oil act by pushing a retina upwards by flotation, within the eye liquid medium. It is because of this that in those cases where retinal injuries that need to be pushed are not placed at an upper location, patients are compelled to maintain and unnatural position for several days. This obvious discomfort for a patient may create work disability and, frequently, major musculoskeletal sequels, all of this provided the patient strictly abides to his positioning, what is being achieved in less than 50% of the cases; thus the procedure success rate being reduced. Because of the same reason, when the injuries are inferior, only in some cases an aberrant position achieves therapeutic usefulness. For the remaining cases with inferior injuries, internal tamponades are not effective. There exist composite silicone oils having a density higher than water's that permit the tamponading of inferior injuries, but leave uncovered upper injuries.

When they get into contact with crystalline posterior capsule, both gas tampons and silicone oil firstly create a posterior capsule opacification and then, a cataract, this making necessary new surgery to replace the crystalline few weeks or months later.

The use of these tamponades may lead to a partial vision loss or even to glaucoma blindness. In the specific case of gas tampons it is difficult to predict their expansion capacity, which varies according to the diverse concentrations and different individuals.

Thus, a sudden and excessive expansion of a gas tamponade may rapidly take intraocular pressure to values higher than the pressure of the arteries supplying the retina and the optic nerve, this leading to tissue death by an ischemia of those structures.

Although the use of oils may create a sudden pressure increase with an ensuing risk of blindness by the blocking of the internal circulation of fluid, it also takes place a pressure increase due to the blocking of aqueous humor outflow by oil bubbles in the Schlemm's canal.

In some patients, silicone oil creates corneal degeneration, because of which a transplant is required as a sole possible way to recuperate a useful vision.

Lastly, a characteristic common to both tamponading forms is the visual disability created while the tamponade remains in the eye. In the case of gas tamponades, these disappear by themselves within a period of 2 to 6 weeks, time during which vision is extremely impaired by the use of the tamponade. On the other hand, in the case of oil its use is not recommended for more than 6 months, during which vision may be extremely impaired. This not only impacts on the work life of treated patients, but on their social life as well. By the same token, beyond this period oil complications (such as the creation of cataracts and glaucoma) are very frequent.

The prolonged use of intraocular oil has shown that oil ends up infiltrating the inner layers of the retina, this having unknown effects on its functioning.

To store silicone oil longer than two months may bring about its emulsfication: this consists of the formation of very small bubbles starting from the large oil bubble. These small bubbles agglomerate and form a white-colored level, similar in aspect to foam, that interfere with vision completely if they reach the visual axis.

On the other hand, another important limitation of gas tamponades is the impossibility of traveling on an airplane, since the sudden expansion created by the atmospheric pressure drop may lead to blindness before the patient descends to sea level.

An additional disadvantage to the utilization of silicone oil tamponades is that in pseudophakic patients, that is to say those patients with intraocular lenses, oil attaches to the lenses surfaces and remains there even after it is extracted. Thus, said oil bubbles may definitely alter the lens optical quality and, consequently, patient's sight.

In the previous art we find the US patent application 2005/0203333 A1, where it is disclosed the utilization of magnetic nanoparticles for the treatment of retinal detachment: "Magnetized scleral buckle, polymerizing magnetic polymers and other magnetic manipulations in living tissue". In particular, in said document it is disclosed the use of magnetic nanoparticles in a medium that polymerizes inside the eye, creating a compact solid that is then attracted by a permanent magnet with a specific shape of a 360° ring (scleral buckle). According to said disclosure, the fluid, once polymerized inside the eye, gets its definitive shape. It is because of this that once the scleral buckle is removed, the polymer persists in the inside without adapting to the eye wall profile. If for any reason the polymer happened to be not effective and the retina detached again, the polymer would remain inside the eye as a foreign body, what would hinder a subsequent surgical operation. ocular.

BRIEF DESCRIPTION OF THE INVENTION

The present invention relates to a material for medical use that comprises biocompatible nanoparticles having superparamagnetic properties, where the superparamagnetic properties of said nanoparticles are employed to localize their action in a determined space or tissue.

In particular, said nanoparticles having superparamagnetic properties are composed of an iron oxide that, among others, may of preference be magnetite. The material according to the invention has various applications, both in surgical and therapeutic treatments.

DETAILED DESCRIPTION OF THE INVENTION

Figure 1:
FIG. 1 shows a retinography of right eye, 7 days after the inoculation of the nanoparticles according to the invention. It can be seen the deposition of the particles onto the retina. The deposition area onto the retina corresponds exactly to the zone where the magnet was implanted behind the rabbit eyeball.

The present inventors propose the use of nanomagnetic tamponades to solve the therapeutic needs with the same effectiveness currently used tamponades have, but without the limitations, unwanted adverse effects, complications and risks current tamponades have.

To do that, the inventors propose the utilization of a magnetic force created between an outer magnet and a biocompatible substance internally used, that may exert on the retina a force equal to, or stronger than, the one supplied by gas or oil tamponades.

To that purpose, in a particular embodiment of the invention, on the outside of the eye and against the sclera it is placed a permanent magnet that may be made of rare earths, alnico or another magnetic material, duly coated to guarantee its biocompatibility. On the inner side, superparamagnetic nanoparticles are used. The importance of particles being paramagnetic lies on the fact that they only exhibit magnetic activity when they are within the influence of a magnetic field. Once this field ceases to exert its influence on them, the nanoparticles spread apart by mere diffusion in the medium. On the other hand, particle composition or coating must be inert and permit the suspension in the vitreous humor liquid medium.

The material according to the invention has a great number of potential uses in therapeutics and surgery. In a particular embodiment, it has shown to be particularly useful for the treatment of retinal detachment.

In trials on animals, the present inventors have been able to prove that the injection of the nanomagnetic tamponade according to this invention permits the maintenance of the retina applied against the eye wall during the whole period when the magnet is kept on the outer side.

The force nanoparticles exert is adjustable according to the mass of the particles and the force from the element that is implanted on the external side, this permitting to increase the force within a pressure range that in its weakest end is similar to the force exerted by the tamponades currently in use.

In conventional treatments, the pressure exerted, for example, with a gas bubble that has a volume equal to one third of the eye volume, is 326 dyn/cm², approximately. By way of comparison, calculating the gradient of magnetic field generated by a permanent magnet shaped like a disk 8 mm in diameter and 0.5 mm high, made of NdFeD and acting upon 1 mg of magnetite cubic nanoparticles 13 nm wide having a saturation magnetization of 35 emµ/g and at a distance of 2 mm (approximately corresponding to a sclera typical thickness), a calculated pressure of 315 dy/cm² is achieved. This calculation shows the feasibility that the retina be tamponated by the effect of magnetic nanoparticles with pressures comparable to those achieved with traditional methods, although without their adverse effects. Also, the inventors have discovered that by varying the quantity of nanoparticles and the configuration and composition of the magnet, it will be possible to work with diverse size and shape tamponades in every region where they may be needed inside the eye.

A tamponade according to the invention may exert its action equally in upper injuries and lower injuries, since its action does not depend on gravity. This sole characteristic would be enough in itself to make the comparative advantage of the nanomagnetic tamponade worthwhile, since most retinal detachments that do not evolve favorably have lower localizations, that are out of reach for ordinary tamponades.

While the tamponade according to the invention exerts its action, transparent media are not altered, and so the quality of vision is not altered. This would reduce the morbidity and the work and social disabilities currently created by the retinal surgery that utilizes usual tamponades of the previous art. It does not limit the use of air transport means either.

On the other hand, in tests performed on animals, no sign of toxicity at the histology level has been seen, weeks after the permanence of the nanoparticles in the intravitreous space in contact with the retina. Their removal would be unnecessary, thus becoming avoidable the need of a second surgery for their extraction.

In another respect, one of the difficulties therapeutic substances used in ophthalmology, and in medicine in general, have is the difficulty of keeping the active principles in a sufficient concentration near the tissue or place that is the objective of the treatment. The superparamagnetic nanoparticles of the invention may bind to proteins, antibodies, radioactive material and every other principle having a therapeutic action and, because they are guided by a magnetic field, they can localize and restrict their action to a determined space or tissue.

According to this invention, it is understood that magnetic nanoparticles (NP) are those particles having a size smaller than 50 nm and show a permanent magnetization. In preferred embodiments, the material according to the invention comprises magnetic nanoparticles with a size ranging from 10 nm to 20 nm and who show a superparamagnetic behavior at room temperature. In another embodiment, the biocompatible nanoparticles have a size ranging between nearly 10 nm and nearly 20 nm and show a superparamagnetic behavior at room temperature. Said superparamagnetic particles must be able to undergo attraction by the magnet to be used and must be biocompatible.

In particular embodiments of the invention, nanoparticles composed of iron oxides, of which it has been shown that have a proven biocompatibility, are used. Even more particularly, from among the iron oxides, magnetite is preferred because this compound shows a higher saturation magnetization or, in other words, because when at equal sizes, said material exhibits a higher magnetization.

An expert in the art will recognize that within the scope of the invention it is also included a material for medical use that comprises nanoparticles composed of a non-biocompatible material, provided those nanoparticles are coated by means of a convenient coating that isolates them from the tissues. Among the materials of this kind that may be utilized are, but are not limited to, cobalt ferrite and the rare-earth alloys (NdFeB, SmCo, and the like). Also the coating that isolates them from the tissues may be constituted by a coating that comprises a material selected from, for example, gold, diamond and inert silica.

In a particular embodiment, prior to being applied, the nanoparticles are suspended in a liquid that is biocompatible with the tissues to be repaired. For example, in the particular case of the utilization of the material according to the invention to repair the retina, the material may be suspended in an aqueous medium. Said aqueous medium might also comprise additives, such as, for instance, hyaluronic acid, methylcellulose and the like. By the same token, in order to achieve a better suspension of the nanoparticles in the liquid medium or to improve their pharmacokinetics or to achieve both things at a same time, said nanoparticles may be coated with a biocompatible organic material. In particular, coatings that include low-molecular weight polysaccharides such as Dextran, Polyethilene glycol (PEG), Poly(oxyethylene)-dicarboxylic acid (polyethylene glycol with carboxylic group bound to the extremities—POE), and the like.

For the utilization of magnetic NP's with medical purposes it must be borne in mind that their size distribution must be very narrow: that is to say, that particle size must be mostly within the average size. To achieve this characteristic and its later suspension in the liquid compatible with the treatment, the NP's are prepared following a chemical pathway: for example, magnetite or cobalt ferrite particles may be prepared from organic precursors in the presence of surfactants, with the purpose of controlling particle size (see, for example, Tailoring the size in colloidal iron oxide magnetic nanoparticles, José M. Vargas and Roberto D. Zysler, Nanotechnology 16, 1474-1476 (2005). After their preparation, the NP's are functionalized with a biocompatible coating that precludes the agglomeration in the suspension and permits their absorption by the tissues.

Nanoparticles must have a size and a magnetization perfectly characterized, in order to be used effectively. The characterization as regards their size may be established through the utilization of transmission or scanning electron microscopy, depending on the equipment resolution at this size level.

The NP's superparamagnetic characteristics and the magnetization value per particle are performed by means of magnetization measurements as a function of magnetic field and temperature, magnetometers being used to that purpose.

The material of the invention may be specially suitable for the treatment of retinal detachment. In that case, in a specific embodiment the magnet that is externally placed on the conjunctiva must have a gradient array of magnetic field, so it may apply the necessary force upon the NP's to direct them onto the tissue to be treated. In the particular case of retinal detachment treatment, this configuration of magnetic field gradient must attract the NP's onto the retina and then exert the force necessary to fix the retina to the eye inner wall in a static way, for the time necessary for the final cicatrization.

In the Spanish patent ES2132029A1, the use of magnetic particles without the superparamagnetic properties proposed in this invention, is disclosed. This difference permits that, because what is being dealt with are superparamagnetic particles, the material according to this invention dilutes when in suspension and is eliminated in the aqueous humor through the trabecular meshwork and Schlemm's canal, until it reaches the bloodstream where, because of their size, the particles create no alterations. On the other hand, the magnetic particles pertaining to the aforementioned antecedent do not exhibit superparamagnetic properties but, on the contrary, they have a permanent magnetism and consequently they remain united as a block. Thus, said material makes it mandatory to maintain the external magnet in its place indefinitely. Should the external magnet be removed, a block of agglomerated magnetic particles would remain inside the eye, as a mobile foreign body, that might create an alteration of vision and unknown consequences for the retina.

Also, the procedure proposed in the aforementioned antecedent patent does not foresee the previous performance of a vitrectomy to extract the vitreous humor and it describes the treatment as a method to apply the retina. According to our experience, a superparamagnetic nanotamponade reaches its peak efficiency when a previous vitrectomy is performed, the retina is applied using the usual surgery methods and the SPM NP's are applied to maintain the retina in its place. The injection of magnetic particles into the vitreous without a previous vitrectomy creates, as shown by our experience, a heterogeneous distribution of the particles that are reached by diverse intensities of the magnetic field from the magnet and find their migration towards the magnet hindered by the resistance offered by the vitreous humor. This causes that in the vitreous humor there remain suspended particles that would create vision difficulties.

The composition of permanent magnets may be ALNICO o rare earths (NdFeB, SmCo and the like). To preclude an interaction with living tissues (in the case magnets are implanted in the organism), magnets may have a coating that isolates them from the tissues, such as a very thin metal coating (nickel, gold, stainless steel and the like) or non-metal (Teflon, surface diamond and the like), inert and stable throughout the treatment period.

The shape and size of the magnets adapts to the treatment area and, in the case of retinal detachment, to the injury that is to be treated. Thus, in particular embodiments, those shapes are circular, elongated, closed, and the like.

The quantity of NP's to be used is dependent on the area and the quantity of tissue that is to be treated. In the case of retinal detachment treatment, the factor establishing the quantity of NP's to be employed is the final pressure said particles exert upon the retina, when this is an immobilization condition upon the eye inner wall: in conventional treatments, the pressure exerted with, for example, a gas bubble, is 326 dyn/cm$^2$ approximately. In the case of magnetite magnetic NP's of ~13. under the action of permanent magnet with the shape of an 8 mm diameter and 0.5 mm high disc made of NdFeB, it is necessary an approximate amount of 14 mg of nanoparticles per cm$^2$ of retina to be covered.

The material of the invention differs from the one disclosed in the US patent 2005/0203333 A1 in that, according to this invention, the particles are not in a polymeric material but at all times they are free among themselves. Aldo, according to the invention, the magnet shape has no limits, being able to have a shape and a size similar to the ones of the injury to be treated.

Among others, the advantages of this invention with respect to the methods disclosed in the previous art and, in particular, in the patent US 2005/0203333 are:

a) The nanoparticles used in the material of the invention are superparamagnetic at all times and, when in absence of a magnetic field, they do not agglomerate: they do it under the influence of the magnetic field of the permanent magnet acting in the treatment only. This means that, according to the invention, the nanoparticles agglomerate onto the retina because of the influence of the magnet and, once the treatment finishes and the magnet is removed from the eye, the NP's spread apart and may be absorbed by the eye tissue. Thus, they may go into the bloodstream to be later eliminated. In the case of the aforementioned patent, when the ferrofluid containing the NP's inside polymerizes, this solid remains inside the eye permanently, even after the treatment is finished.

b) Because particles are free and have a large active surface, it is possible to functionalize them with a suitable coating (for example, medications or biologically active material) allowing for the treatment of the disease in an active way, together with using the tamponade effect of the retina. Conversely, this is not possible with the material disclosed in the aforementioned patent, because when the NP-containing fluid polymerizes, the release of therapeutically active substances towards the tissue is prevented.

c) The shape and size of the magnet are not a limitation for the treatment, since it is possible to place a magnet having no larger a size than the size of the injury to be treated.

The magnetic nanoparticles (NP) composing the material according to the invention may generally be synthesized through a chemistry pathway. As an example of the manufacture of magnetite (and cobalt ferrite) NP's we mention the synthesis from organic precursors such as Fe(acac)3 (and, in the case of cobalt ferrite, with the addition of Co(acac)2 in a stoichiometric ratio) in the presence of surfactants (oleic acid and oleylamine) in diphenyl ether (organic solvent). The formation of NP's takes place at a temperature of 270° C. and the precursor-surfactant ratio permits to control the particle average size with a very narrow size distribution. The product of this synthesis contains a suspension of magnetite (or cobalt ferrite, according to the case) nanoparticles coated with oleic acid that precludes their agglomeration. The coating of these particles may be changed to hydrophileous compounds that permit the particles to be suspended in aqueous media that will also be of interest in the applications for medical treatments, such as, for example, dextran, polyethylene glycol (PEG), poly (oxyethylene)-dicarboxylic acid (polyethylene glycol with carboxyl groups in its extremities—POE and polyethylene imine (PEI).

In the case of cobalt ferrite NP's, since they are not biocompatible they need an inert coating that keeps the magnetic material isolated from the tissues. That is achieved with a gold or silica coating. In the case of gold coating, this is achieved by adding gold salts and a reducing agent to the NP aqueous suspension in a way such that the nanoparticles play the role of seeds for the formation of metallic gold onto them, thus a cobalt ferrite NP's coated in gold is being achieved.

In the case of making a silica coating, it is performed by adding, to the NP's suspension the necessary quantity of tetrasiloxane (TEOS), that is the silica precursor. The end product is a suspension of magnetic NP's coated in inert silica.

Figure 4:
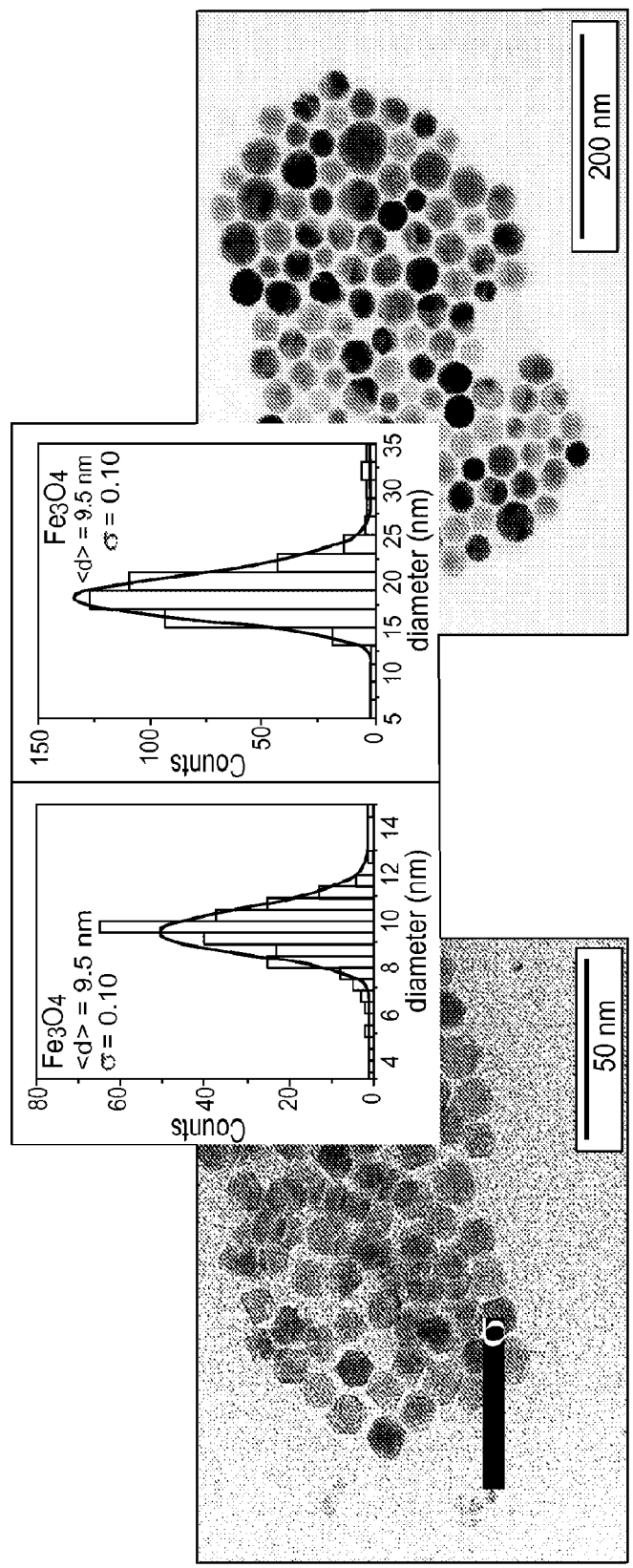
FIG. 4: Images of magnetite particles from two different syntheses taken by transmission electron microscopy are shown: it is seen that each nanoparticle is constituted by a single magnetite crystal having an average size defined with a narrow distribution of sizes, as it is seen from the histograms.

The NP's thus synthesized may be characterized morphologically and magnetically. The morphological characterization consists of the performance of an X-ray diffractogram of an NP dry powder, by means of which the composition and crystal phase of the NP's is confirmed. The NP size and shape is established by means of transmission electron microscopy: for example, in FIG. 4 histograms of size distribution for magnetite NP's from diverse syntheses are shown. The magnetic characterization, that establishes the magnetization of the material, hence the interaction the NP's will have when an external magnetic field is applied, is carried out, by means of a magnetometer, from the magnetization curves as a function of the applied field.

All of the suspensions prepared and ready for use employ a solvent as an aqueous medium. This solvent may consist of water or a physiological solution, or else have the necessary additions that are characteristic of the medical treatment to be performed such as, for example, some medication. The NP's thus prepared are kept naturally in suspension and neither flocculate nor agglomerate because of the existence of the coating that was added to them.

With the purpose that these NP's may be utilized as media for medical treatments, the suspension has to be sterilized. This is done in a conventional autoclave. The heating of the suspension does not alter the NP nature, since they are synthesized at higher temperatures than those at which an autoclave works and the molecules coating the NP's do not degrade at said temperatures.

According to this invention, the SPM NP's are injected in suspension, but act by themselves, without changing state nor creating polymers or adopting forms. They maintain themselves joined to each other in their position onto the retina while the magnetic field acts upon them. When this field disappears because the external magnet is extracted, the particles disperse in the intraocular space.

Thus, the advantages of using the material comprising superparamagnetic (SPM) nanoparticles (NP) according to this invention for the treatment of retinal detachment, when compared to gas or silicone oil tamponades that are of ordinary use in surgery are:
the SPM NP's do not create cataracts,
the SPM NP's do not create glaucoma,
the SPM NP do not depend on the injury location: they are equally efficient on upper and lower injuries,
they do not require a mandatory second surgery,
magnetite is inert and does not exist a peremptory extraction deadline.

The comparative advantages of this invention with regard to what was disclosed in patent application US 2005/0203333 A1 are, among others:
the SPM NP's do not polymerize,
they do not turn into a solid or a dense fluid,
the implanted magnet may be extracted without leaving a solid inside the eye cavity,
they can be extracted easily by means of surgery
they can simply be left to diffuse into the aqueous humor, when the external magnet is extracted,
they do not interfere with sight, should the external magnet be extracted.

EXAMPLES

Example 1

For the stage of preclinical experimentation, the effectiveness of the material underwent trial on cadaveric eyes of pig and in vivo eyes of rabbit.
a) Trial on pig cadaveric eyes. 10 pig eyes were used.
The conjunctiva was dissected from the sclerocorneal limbus, until the sclera was exposed. Afterwards, the anterior segment of the posterior part of the cup, to facilitate the image recording of tamponade action and verify that the theoretical calculation could be reproduced experimentally.

Variable-shaped rare earth magnets were implanted. In the following example, an annular magnet with a 5 mm diameter and 2 mm thickness was used.

The magnets were adhered to the sclera with cyanoacrylate. Then the detachment of the retina was induced and the retina portion covered by the SPM NP's was kept applied in all cases.
b) In vivo trail on rabbit eyes
10 albino New Zealand rabbits and 10 pigmented Californian rabbits were utilized.
10 pigmented New Zealand rabbits and 23 white ones with weights ranging from 2.5 to 3 kilograms, kept in light/darkness cycles of 12 hours with food and water ad libitum. The animals were kept and treated according to the regulations and protocols approved and established by ARVO.

Each animal was anesthetized with 3 ml from a mixture of 2.5 ketamine (125 mg) and 0.5 ml of xylazine (100 mg).
A surgical intervention was performed on the right eye of each animal.
Surgical Procedures
1) Group 1
Objective
To prove in vivo that the superparamagnetic particles act in an effective way as an in vivo tamponade.
Materials and Methods
A surgical intervention was performed on the right eye of each animal.
In the intervention it was performed the aperture of the conjunctiva from the sclerocorneal limbus at lower 180°, using Wescott scissors. The Tenon's capsule was dissected until leaving the sclera surface free and dry, to implant a rare-earth nickel-coated magnet having a circular shape 5 mm in diameter, 1.5 mm in thickness and a 2 mm-central hole. The sclera was fixed with two suture points with Vicryl 7-0 in the eye temporal side, behind the equator of the eyeball.

The operated eyes were dilated with 3 drops of 1% phenylephrine and 2% tropicamide on the cornea was placed a plano-concave contact lens to watch the posterior pole of the eye.

The operated eye of the rabbit was watched under microscope with coaxial light.

In order to show through the microscope the precise place for the injection of particles, the implanted magnet was indented by pushing from the outside with titanium tweezers, to avoid magnetization.

The particles, with a 10% concentration and 100 microliters volume, contained inside a 1 mm syringe, were injected at the pars plana, at 2.5 mm from the limbus, with a 27 G needle. Afterwards, the particles were released inside the eye from a distance of less than 3 mm from the corresponding retinal surface, the magnet being placed on the external side.

The nanoparticles remained inside the eye for 4 weeks. On the days 3, 7, 14, 21 and 28 the animals were assessed under anesthesia, microscopes being used to find signs of inflammation in the anterior chamber of the eyeball or in the vitreous. Photographs were taken for the records. The animals were sacrificed on the day 28, their eyes were enucleated, fixed in 10% formol, embedded in paraffin, cut with a microtome to a thickness of 7 µm, stained with haematoxilin-eosin and watched through microscope at 10× and 40×.
Results
During the application of the NP's it was noted that they move towards the retinal surface, uniformly arranging themselves on the surface corresponding to the external magnet.

In the following observations they remained in their place and position without dispersing. No signs of inflammation were noted in the clinical assessments.

Retina histological analysis showed an absence of inflammatory compromises. The retina that was in contact with the particles maintained its thickness unaltered, in relation to the free retina. No structural damage because of compression was noted.

Figure 2:
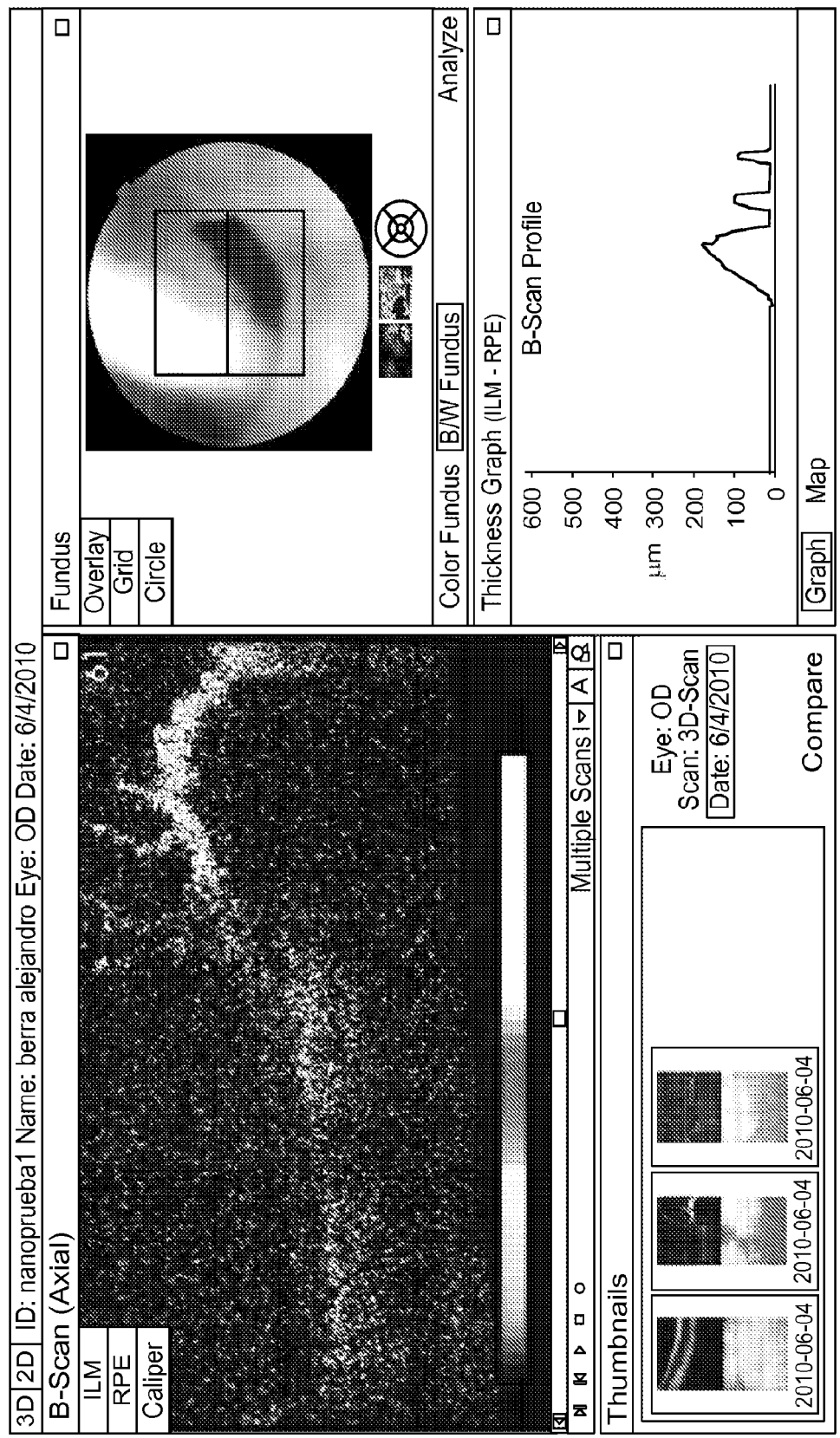
FIG. 2 shows an optical coherence tomography (OCT) of the same eye and rabbit as those in FIG. 1, 1 to 7 days after the inoculation of the nanoparticles according to the invention. At the upper right corner it is seen the retinography with a green-line box framing it. In the center of the box it is seen a green line that marks the delimitation zone of the optical coherence laser. At the left it is seen the retinal layers as taken by the passage of a laser light: the nanoparticles onto the retina that preclude the laser light penetration into the retinal layers are seen; then, the retinal layers where there are no nanoparticles.
Figure 3:
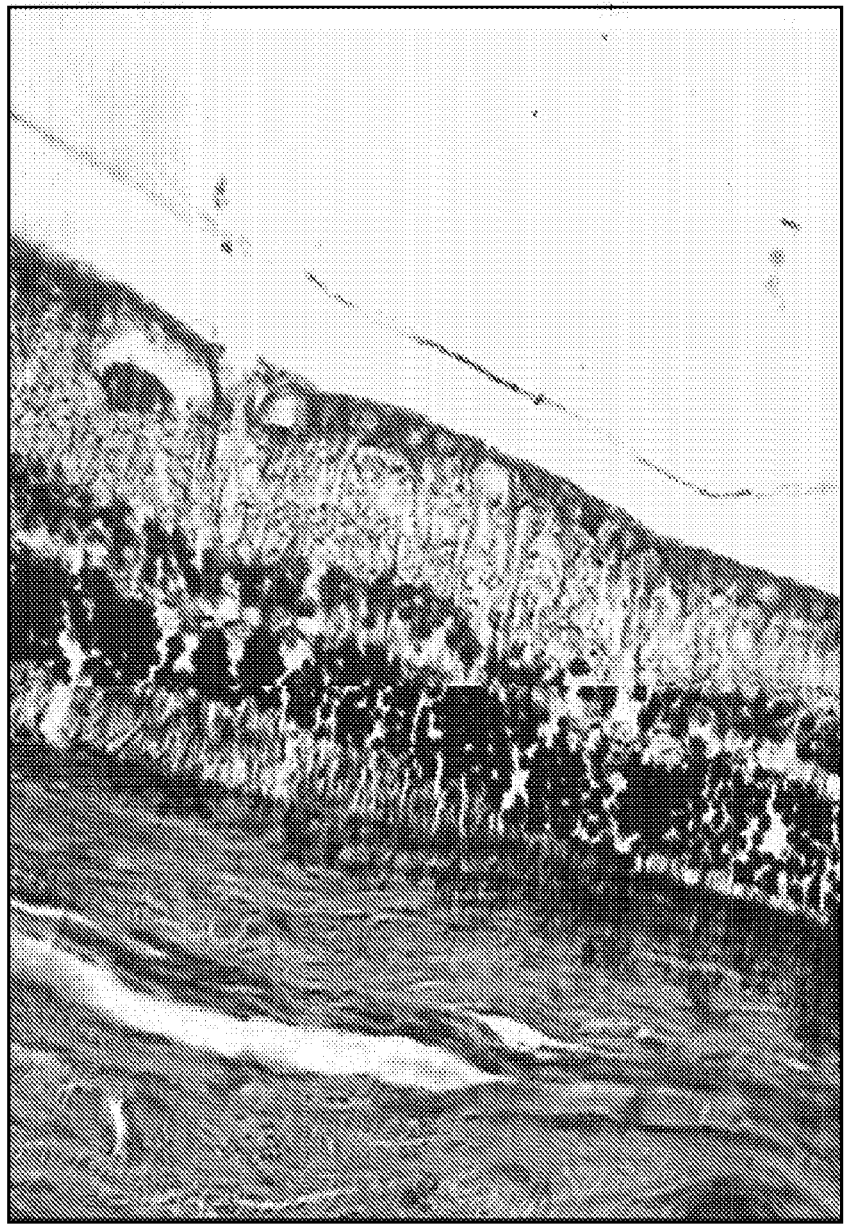
FIG. 3: The histology of the same eye and a rabbit's, as in FIG. 1, is shown 28 days after the inoculation of the nanoparticles according to the invention.

In FIGS. 1 and 2, images of NP's deposited on the retina in a semicircular disposition are seen, this disposition corresponding to the position of the magnet contacting the external eye surface.

This was seen in the 10 animals on the days 3, 7, 14, 21 and 28.

The animals were watched in the 4 subsequent weeks.

During the clinical observation through microscope, no inflammatory reactions were detected.

In the study of the histological samples no signs of inflammation or tissue damage were noted. No intrusion of particles between retinal layers was noted.

2) Group 2

A procedure similar to the abovementioned one was performed, different magnets with or without indentation having been used.

3) Group 3

A procedure similar to the abovementioned one was performed, with fixation to the sclera with cyanoacrylate adhesives.

4) Group 4

A procedure similar to the abovementioned one was performed, the same substance and with the addition of 1% hyaluronate having been used.

5) Group 5

Objective

To prove the effectiveness of the SPM NP's to maintain the retina applied, in a rabbit model of retinal detachment.

Materials and Methods

In this group, once anesthetized 3 rabbits and a magnet placed on the external sclera in the same procedure, a vitrectomy was performed. Three incisions were made on the sclera with a V type Lance sclerotome 1 m wide. In one of the sclerotomies a Ringer infusion cannula was inserted; in the other, a endoilluminating probe was inserted and in the third one, a vitrectome point. By approaching the point to the retina and increasing the aspiration, it was possible to tear the retina. With a subretinal infusion cannula, liquid was injected underneath the retina, until completion of the detachment. The observations were carried out following the same protocol as in 1 and a histological study of the samples was performed.

Results

In the three cases it was seen that the particles kept the tear occluded and applied, whereas the retina, on day 7, remain applied in all the cases.

Example 2

Examples of Performances with Magnetic Nanoparticles in Medical Applications

Magnetite superparamagnetic nanoparticles (NP) with sizes ranging between 10 and 20 nm in diameter, coated with Polyethylene glycol (PEG) and Poly(oxyethylene)-dicarboxylic acid (polyethylene glycol with carboxyl groups in its extremities—POE), in tissues. The polysaccharide coating is biocompatible. At this size and with these coatings it may be unnoticed by the patient's immunological system, for the period necessary for the treatment to be performed.

Said nanoparticles were utilized in animal models for:

The repair of retinal detachment using the magnetic force between the NP's and a permanent magnet attached to the outside of the eyeball.

The treatment of tumors by hyperthermia. These nanoparticles have the ability to bring about an NP endocytosis by tumor cells. After the endocytosis, these NP's are heated under the action of an alternate magnetic field, thus producing the necrosis of the tumor cells by hyperthermia.

The transport of antibodies, proteins and plasmids, or all of these at a same time. Magnetic nanoparticles coated with POE may be utilized for medical treatments comprising the administration of the abovementioned active substances. The carboxyl groups that are set free from the POE molecules extremities are active for the incorporation of antibodies, proteins or plasmids, or the three of them together, to be used to repair particular tissues. This set NP-medication is directed within the organism by means of the application of an external magnetic field designed to that purpose. Thus, the treatment is directed by the interaction magnetic NP—magnetic field towards the tissue to be treated, with the consequent advantage of selectivity for the treatment.

Superparamagnetic magnetite or cobalt ferrite nanoparticles (NP), with sizes ranging from 10 to 20 nm in diameter, coated in gold. This coating is stable and inert to the organism, what enables its utilization in medical treatments. A gold surface has a great affinity for sulphur-containing molecules, since a sulphur-gold bond is strong. An example of that is the case of using a thiol coating on gold: the system magnetic NP-Gold-thiol constitutes an ideal platform to attach medication that can be directed towards a specific tissue by means of an external magnetic field created to that purpose. An example of the utilization is chemotherapy.

Superparamagnetic magnetite or cobalt ferrite nanoparticles (NP), with sizes ranging from 10 to 20 nm in diameter, coated in silica. This coating is stable and inert to the organism, what enables its utilization in medical treatments. A silica surface has a great affinity for polysaccharide molecules or for molecules having OH groups available to bind with silica. the system magnetic NP-silica constitutes an ideal platform to attach medication that can be directed towards a specific tissue by means of an external magnetic field created to that purpose. Examples of this platform are:

Chemotherapy in the case of attaching a specific medication.

The treatment of tumors by hyperthermia, in the case of attaching a polysaccharide or an antigen specific for the tumor to be treated.

Example 3

Generally, magnetic nanoparticles (NP) are synthesized through a chemical pathway. As an example of the manufacturing of magnetite (and cobalt ferrite) NP's, we may mention the synthesis from organic precursors, such as Fe(acac)3 [and, for the case of cobalt ferrite, with the addition of Co(acac)2 in a stoichiometrical ratio) in the presence of surfactants (oleic acid and oleylamine) in ether (organic solvent). The formation of NP's takes place at a temperature of 270° C. and the precursor/surfactant ratio permits to control the average size of the particles, with a very narrow size distribution. The product of this synthesis contains a suspension of magnetite (or cobalt ferrite, as the case may be) coated in oleic acid, what precludes their agglomeration. The coating of these particles may be changed to hydrophileous that permit the particle suspension in aqueous media that are also of interest in the applications for medical treatments such as, for example, dextran, polyethylene glycol (PEG), carboxyl-polyethylene glycol (POE), polyethylene amine (PEI).

In the case of cobalt ferrite NP's, since they are not biocompatible they need an inert coating that maintain the magnetic material isolated from the tissues: this is achieved with a gold or silica coating. In the case of gold coating, this is achieved approaching gold salts and a reducing agent to the NP aqueous solution, in a way such that the nanoparticles play the role of seeds for the formation of metallic gold on the nanoparticles, a suspension of cobalt ferrite NP's coated in gold being achieved.

In the case of performing a silica coating, that coating is carried out adding to the NP suspension the necessary quantity of tetraethoxysilane (TEOS), that is the silica precursor. The end product is a suspension of magnetic NP's coated in inert silica.

The NP's thus synthesized are morphologically and magnetically characterized. The morphological characterization consists of the performance of an X-ray diffractogram of an NP dry powder, what confirms both composition and crystal phase of the nanoparticles. Their size and shape are established by means of transmission electron microscopy. By way of example, distribution histograms for the size of magnetite NP's from diverse syntheses are shown. The magnetic characterization, that establishes the magnetization of the material, hence the interaction the NP's will have with an applied external magnetic field, is carried out by means of a magnetometer, from the magnetization curves as a function of the applied field.

All of the suspension prepared and ready to be used use, as a solvent, an aqueous medium, that may be water or a physiological solution or else have all the necessary additions characteristic of the medical treatment to be performed, such as, for example, a medication.

The NP's thus prepared are naturally kept in suspension and neither flocculate nor agglomerate because of the existence of the coating that was added to them.

With the purpose that these NP's may be utilized as a medium for medical treatments, the suspension has to be sterilized. This is done in a conventional autoclave. Heating the suspension does not alter the NP nature, for the nanoparticles are synthesized at temperatures higher than those at which the autoclave work and the molecules coating the NP's do no degrade at these temperatures.

What it is claimed is:

1. A procedure for tamponading a patient's retina, comprising the following steps in order:
    i. submitting the patient to a vitrectomy;
    ii. injecting a material into the patient's intravitreous space, wherein the material is in the form of a liquid suspension comprising biocompatible nanoparticles having superparamagnetic properties, and the liquid suspension does not contain a polymeric material; and
    iii. through application of a magnetic field created by a magnet located outside the eye, attract the nanoparticles to push and maintain the retina applied against an inner wall of the patient's eye,
        wherein a step of polymerizing the nanoparticles does not take place between steps ii and iii.

2. The procedure according to claim 1, wherein the nanoparticles may exert their action equally for upper injuries and for lower injuries.

3. The procedure according to claim 2, wherein the nanoparticles are injected together with a pharmaceutically acceptable vehicle or carrier contained in the liquid suspension or in a composition separate from the liquid suspension.

4. The procedure of claim 1, further comprising the steps of
    iv. removing the magnetic field applied in step iii,
    v. allowing the nanoparticles to be absorbed by the patient's eye tissue.

* * * * *